United States Patent [19]
Quinlan et al.

[11] Patent Number: 5,769,775
[45] Date of Patent: Jun. 23, 1998

[54] AUTOMATED CENTRIFUGE FOR AUTOMATICALLY RECEIVING AND BALANCING SAMPLES

[75] Inventors: Michel G. Quinlan; Stephen J. Wright; Lubomir Markov, all of Peterborough, Canada

[73] Assignee: Labotix Automation Inc., Canada

[21] Appl. No.: 777,951

[22] Filed: Dec. 23, 1996

Related U.S. Application Data

[63] Continuation of Ser. No. 686,946, Jul. 26, 1996, abandoned.

[51] Int. Cl.[6] .................................................. B04B 9/14
[52] U.S. Cl. ................................ 494/10; 494/37; 494/82
[58] Field of Search ................................... 494/1, 10, 11, 494/12, 20, 34, 37, 82, 85; 210/144, 363; 74/572, 573 R; 422/72; 436/45, 47

[56] References Cited

U.S. PATENT DOCUMENTS

| | | | |
|---|---|---|---|
| 3,151,073 | 9/1964 | Anthon | 422/72 X |
| 4,332,349 | 6/1982 | Dietrich et al. | 494/10 X |
| 4,927,545 | 5/1990 | Roginski | 494/10 X |

FOREIGN PATENT DOCUMENTS

| | | |
|---|---|---|
| WO 9625712 | 8/1996 | WIPO . |
| WO 9636437 | 11/1996 | WIPO . |

*Primary Examiner*—Charles E. Cooley
*Attorney, Agent, or Firm*—Fitzpatrick, Cella, Harper & Scinto

[57] ABSTRACT

An automated centrifuge includes a weighing station to weigh sample holding racks which arrive at the centrifuge and a rack handling robot to transfer the weighed racks to and from the centrifuge. A controller, which operates the rack handling robot, employs a novel balance method to have the rack handling robot load the sample holding racks in the centrifuge to obtain a best balance arrangement of the sample holding racks. If the balance method determines that the best balance arrangement will exceed one or more predefined balance thresholds, appropriate remedial action is taken by substituting a selected balance rack for a loaded sample holding rack.

20 Claims, 6 Drawing Sheets

AUTOMATED CENTRIFUGE FOR AUTOMATICALLY RECEIVING AND BALANCING SAMPLES

The subject application is a continuation of application Ser. No. 08/686,946, filed Jul. 26, 1996, now abandoned.

FIELD OF THE INVENTION

The present invention relates to a centrifuge for separating the components of liquid samples. More specifically, the present invention relates to an automated centrifuge which automatically receives and loads samples for centrifuging.

BACKGROUND OF THE INVENTION

Centrifuges are used in a variety of processes to separate liquids into their components via centrifugal force. The liquids to be separated can be mixtures, suspensions, etc. and are often held in containers, such as vials or test tubes, which are rotated at high speed by the rotor of a centrifuge. A common use for centrifuges is to separate blood samples into plasma and blood cells for subsequent analysis.

Because centrifuges rotate at high speeds, it is required that the centrifuge rotor and the liquids to be separated be relatively well balanced about the rotational axis of the centrifuge rotor. Some tolerance for off balance conditions is provided by the centrifuge manufacturer's specification of the centrifuge's rotor bearings and other components. However, this tolerance is generally limited and is provided at an increase in the cost of the centrifuge due to the larger bearings, etc.

In many circumstances, the loading of a centrifuge with samples is an empirical activity, with a laboratory technician visually examining samples to be loaded into the centrifuge in an attempt to evenly position the mass of the samples about the centrifuge rotor. For example, if blood samples are to be processed, the laboratory technician will visually examine racks of samples to be loaded, comparing liquid levels in the samples of a rack to those in another rack. When the technician identifies racks which are believed to be of similar mass, as determined by relative liquid levels, they are placed on opposite sides of the centrifuge rotor. As this technique is not very accurate, the centrifuge components are typically over designed to accommodate some imbalance.

Another, and often more significant disadvantage of this technique, is that it requires a substantial time commitment on the part of the technician to load, balance and unload the centrifuge.

SUMMARY OF THE INVENTION

It is an object of the present invention to provide a novel automated centrifuge which obviates or mitigates at least one disadvantage of prior art centrifuges. It is a further object of the present invention to provide a novel method of balancing the sample load of a centrifuge.

According to a first aspect of the present invention, there is provided an automated centrifuge for processing samples loaded into sample holding racks, comprising:
 a weighing station to determine for each rack delivered to said centrifuge the mass of the rack and the center of gravity of the rack, relative to the longitudinal axis of the rack;
 a centrifuge rotor operable to receive and centrifuge a number of sample holding racks;
 a controller to determine a loading arrangement for said weighed racks which results in the balancing of the rotor within predetermined thresholds when said rotor is loaded with said weighed racks; and
 a rack transfer means to load and unload weighed racks in said rotor, said weighed racks being loaded in an arrangement corresponding to said determined loading arrangement.

According to another aspect of the present invention, there is provided a method of determining an arrangement of a preselected number of sample holding racks to be loaded into the rotor of a centrifuge, said arrangement resulting in the balancing of said rotor within one or more pre-defined thresholds when said rotor is loaded with said racks, comprising the steps of:
 (i) weighing a set of racks to be loaded into said rotor, said weighing determining the total weight of the rack and the center of gravity of the rack with respect to the longitudinal axis of the rack;
 (ii) examining said determined total weight of each rack and selecting two subsets of equal numbers of said preselected number of racks, said two subsets being selected such that the difference between the total of the weights of the racks in each said selected subset is less than a pre-defined threshold; and
 (iii) examining each said selected subset to orient the placement of the racks in each said subset such that the net distance of centers of gravity of the racks in a subset from the midpoint of the racks is less than a pre-defined threshold.

According to yet another aspect of the present invention, there is provided a method of loading a centrifuge rotor with a preselected number of sample holding racks in an arrangement which results in the balancing of said rotor within one or more pre-defined thresholds, wherein said rotor comprises two diametrically opposed rack receiving trays, comprising the steps of:
 (i) receiving said preselected number of racks to be loaded in said rotor;
 (ii) weighing each of said received racks, said weighing determining the total weight of the rack and the center of gravity of the rack with respect to the longitudinal axis of the rack;
 (iii) examining said determined total weight of each rack and selecting two subsets of equal numbers of said preselected number of racks, said two subsets being selected such that the difference between the total of the weights of the racks in each said selected subset is less than a pre-defined threshold; and
 (iv) examining each said selected subset to determine the orientation of the racks in each said subset such that the net distance of the centers of gravity of the racks in a subset is less than a pre-defined threshold;
 (v) loading each said rack receiving tray with one determined subset, the racks in each determined subset being loaded in said determine orientation..

BRIEF DESCRIPTION OF THE DRAWINGS

Preferred embodiments of the present invention will now be described, by way of example only, with reference to the attached Figures, wherein.

DETAILED DESCRIPTION OF THE INVENTION

Figure 1:
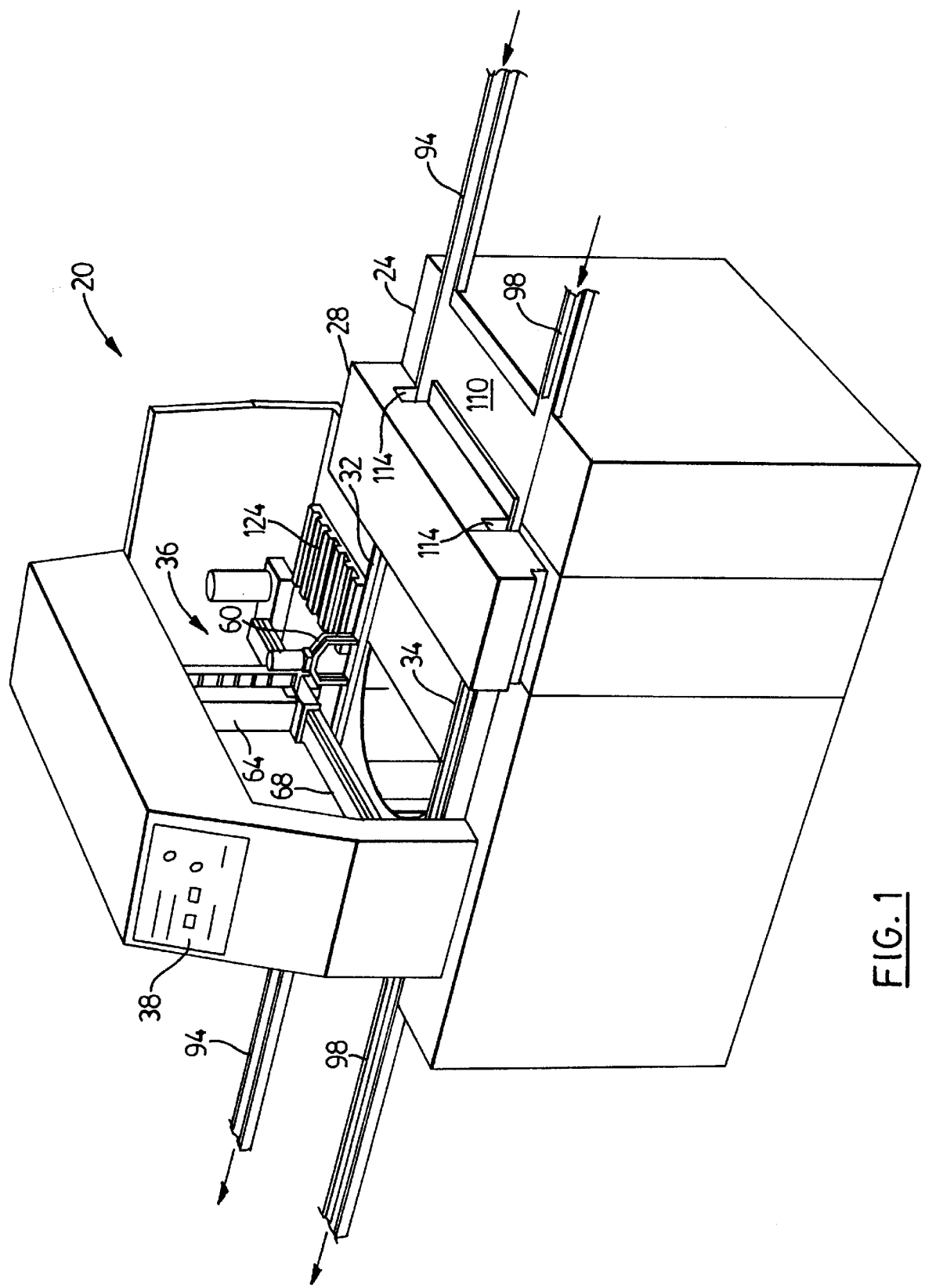
FIG. 1 shows a perspective view of an automated centrifuge in accordance with the present invention.
Figure 2:
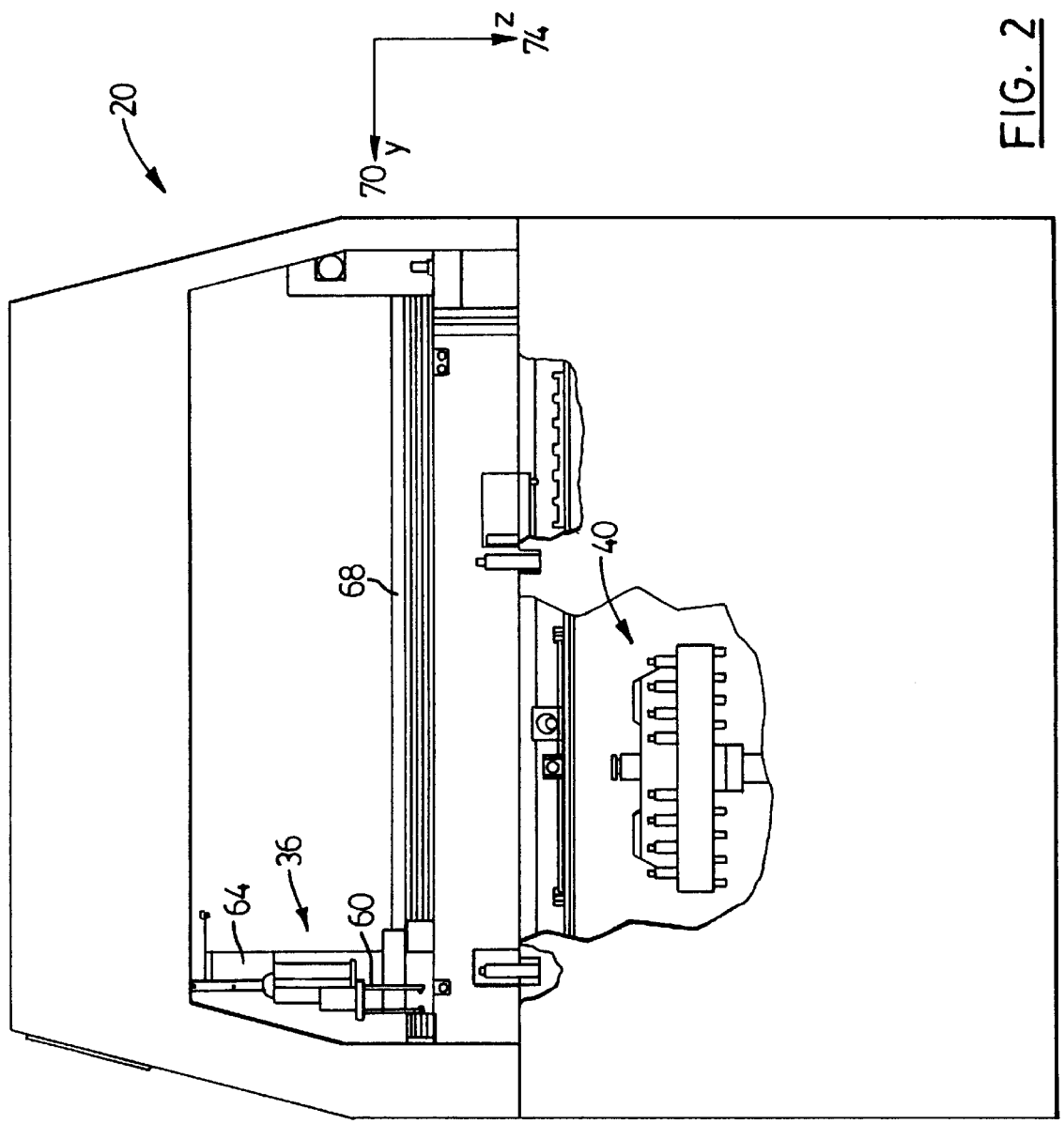
FIG. 2 shows a front view of the centrifuge of FIG. 1 with breakaway sections showing the centrifuge rotor and a parking zone.
Figure 3:
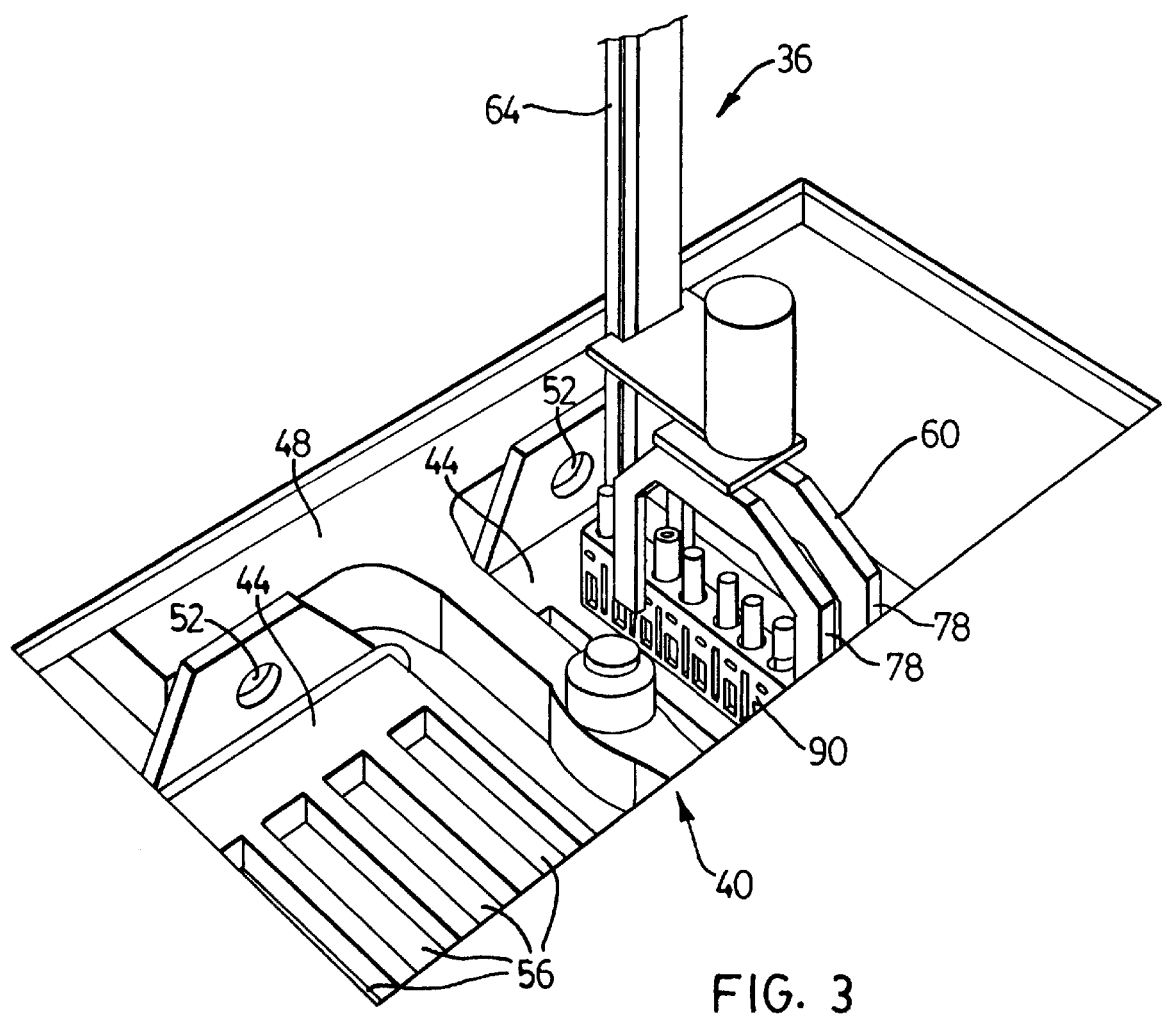
FIG. 3 a perspective view of the centrifuge rotor and a gripper mechanism of a rack handling robot.

An automated centrifuge in accordance with the present invention is indicated generally at 20 in FIG. 1. Centrifuge 20 includes a transfer station 24, a weighing station 28, rack conveyors 32 and 34, a rack transfer means, such as rack handling robot 36, a control means 38, and, as shown in FIGS. 2 and 3, a centrifuge rotor 40. The construction and arrangement of centrifuge rotor 40 is not particularly limited and, in a present embodiment of the invention, rotor 40 and its associated motor drive is a conventional centrifuge mechanism, manufactured by Sorval Inc., 31 Peck's Lane, Newton, Conn. and used in their model RC-3B centrifuge.

As best seen in FIG. 3, rotor 40 includes two four-position rack trays 44 each of which is suspended from a rotor hub 48 by a pivot 52 at each end. Each rack tray 44 includes four slots 56 in which a sample rack can be placed. As will apparent to those of skill in the art, when rotor 40 is in operation, rack trays 44 swing outwardly, due to the developed centrifugal force, and attain a position wherein the bottom surface of slots 56 are substantially vertical.

Rack handling robot 36 comprises an electrically actuated parallel gripper 60, best seen in FIG. 3, which is mounted to a vertical actuator column 64, best seen in FIGS. 1 and 2, which is in turn mounted to a horizontal track 68. Rack handling robot 36 is operable to move gripper 60 in the y-axis (arrow 70 in FIG. 2), horizontally along track 68, and in the z-axis (arrow 74 in FIG. 2), vertically on column 64. Accordingly, rack handling robot 36 is operable to have gripper 60 engage a holding rack of samples delivered on rack conveyor 32 and to lift the rack vertically off of conveyor 32, move the rack horizontally to a position above a selected one of slots 56 and to lower the rack vertically into the selected slot 56.

Figure 4:
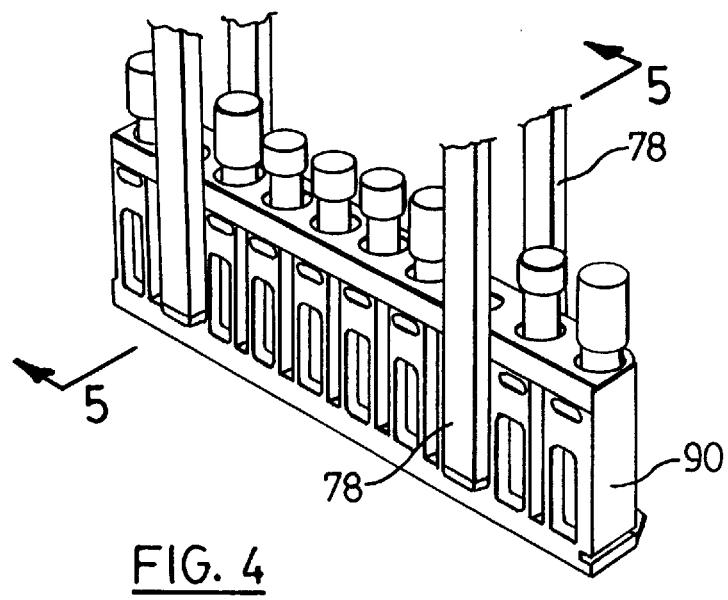
FIG. 4 shows the gripper mechanism of FIG. 3 engaging a sample holding rack for use therewith.
Figures 5, 6:
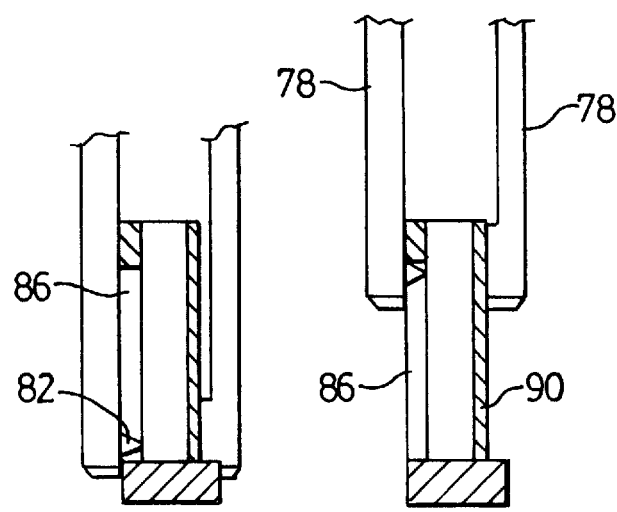
FIG. 5 shows a view taken along line 5-5 of FIG. 4 wherein the gripper mechanism is engaging the sample holding rack in an over travelled position.
FIG. 6 shows the gripper mechanism and sample holding rack of FIG. 5 wherein the gripper is at the engagement position of the sample holding rack.

As best shown in FIGS. 4 and 5, it is presently preferred that gripper 60 not rely upon friction to maintain a sample holding rack in gripper 60 but instead rely upon two sets of opposed pairs of fingers 78, at least one of these pairs of fingers 78 including a boss 82 which engages a groove 86 in the sample rack 90 as shown in FIGS. 5 and 6. The placement of boss 82 into groove 86 prevents rack 90 from slipping out of gripper 60, as shown in FIG. 6, but allows rack handling robot 32 to over travel vertically, as shown in FIG. 5, as it places rack 90 into a slot 56 or onto any other surface.

As discussed in more detail below, in balancing the loading of sample holding racks into rotor 40 it is desired to be able to position the end to end center of gravity of the rack according to balancing criteria. Accordingly, a rack will be inserted into a slot 56 in either a first orientation or a second orientation, rotated one hundred and eighty degrees. In a present embodiment of the invention, rotor 40 can be positioned accurately in, and easily moved between, the position shown in FIG. 3 and the mirror-image position. Thus, rotation of gripper 60 to reverse the loading orientation of a rack in a slot 56 is not required and the effective rotation of a rack with respect to a slot 56 is accomplished by rotating rotor 40 to the mirror-image position before loading the rack into the selected slot 56. For example, if in FIG. 3, rack 90 can be inserted into the second slot 56 from the rotor center in the right hand rack tray 44 as shown, or rotor 40 can be rotated 180 degrees and rack 90 inserted by robot 36 into the same slot 56 which is now the second slot from the rotor center on the left hand rack tray 44. Of course, if it is not desired to rotate rotor 40 while loading racks, gripper 60 can be equipped with means to rotate it through 180 degrees.

Control means 38 is not particularly limited and in an embodiment of the present invention is a computer controller based on an Intel Pentium microprocessor and having an operator display screen and data input device (not shown). Control means 38 includes a robot controller card, such as a PMAC-PC card, Part Number 400-602204-10X, manufactured by Delta Tau, 9036 Winnetha Ave., Northridge, Calif., which is used to control the operation of rack handling robot 36. Control means 38 also operates to balance the loading of sample holding racks in centrifuge 20, as is described below in more detail.

As shown in FIG. 1, sample holding racks are delivered to and removed from centrifuge 20 via one of two transport systems 94 and 98. Transport systems 94 and 98 may be any suitable system for delivering and removing sample holding racks from centrifuge 20, and in the embodiment shown in FIG. 1 comprise a conveyor track system.

Transfer station 24 includes a conveyor 110 which is operable to transfer a sample holding rack from transport system 94 to transport system 98, or vice versa, as desired. This allows, for example, sample holding racks which arrive via transport system 94 when centrifuge 20 is centrifuging a set of racks to be transferred to transport system 98 which can then convey the racks to another centrifuge unit (not shown) which is free to accept them.

As mentioned above, it is important that rotor 40 and the samples loaded in to it be substantially in balance before rotor 40 is brought to centrifuging speed. As also mentioned above, in centrifuge 20 this balancing is accomplished automatically, as is described below.

Figure 7:
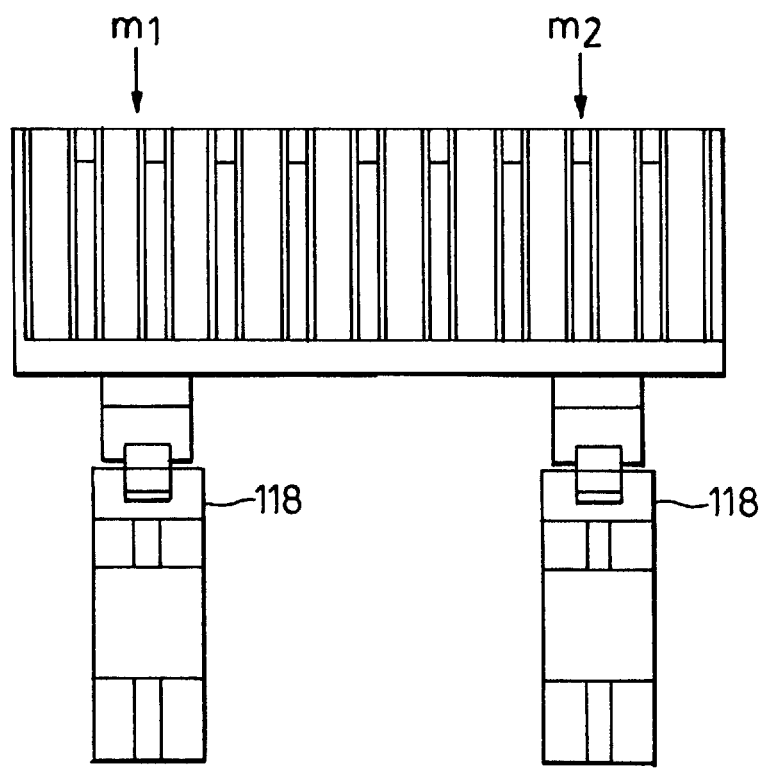
FIG. 7 shows a sample holding rack being weighed.

When a sample holding rack arrives at centrifuge 20 via one of transport system 94 or 98 or if delivered by hand by a technician, it is weighed in weighing station 28. Specifically, a conveyor moves the sample holding rack into a respective one of the weigh sites 114 in weighing station 28. The sample holding rack is then weighed by a spaced pair of load cells 118, as shown in FIG. 7 which determine its overall weight and its center of gravity about its longitudinal axis from measurements $m_1$ and $m_2$. When the weight information has been determined, the sample holding rack is moved by rack conveyor 32 or 34, as appropriate, to a position wherein it may be engaged by gripper 60. Rack handling robot 36 then positions the sample holding rack into one of slots 56 in rotor 40, the particular slot 56 selected being determined by the balancing method described below. While the following discussion deals with a rotor which can hold eight sample racks, the present invention is not so limited and can be employed with centrifuges which process more or fewer racks, as will occur to those of skill in the art.

Figure 8:
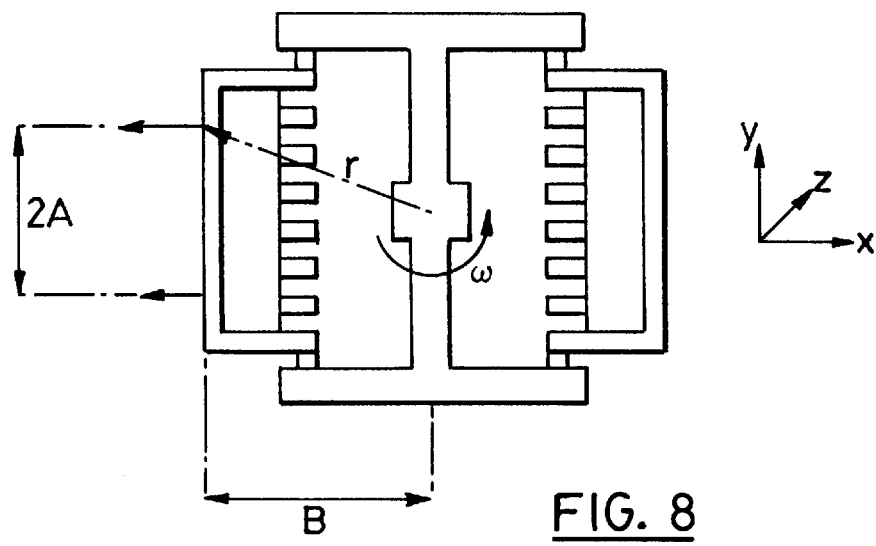
FIG. 8 shows a schematic representation of the rotor components when operating.

A discussion of the method of loading centrifuge 20 in a substantially balanced manner will now follow, with reference to FIG. 8 which shows a schematic representation of the rotor 40 in use with rack trays 44 pivoted outwardly. In this embodiment of the present invention, wherein eight sample holding racks are loaded into two rack trays which each hold four sample holding racks, it can be shown that there are 2,580,480 different arrangements in which the sample holding racks can be loaded into centrifuge 20. Clearly, considering each of these arrangements, in a brute force analysis technique, is undesirable and a less computationally expensive method has been developed by the present inventors and is described below.

As is well known, the centrifugal force which results from a body being rotated about an axis is given by equation (1) in Appendix A, where F is the resulting force, m is the mass of the body, $\omega$ is the angular velocity of the body and r is the distance from the axis of rotation to the center of mass. Equation (2) in Appendix A determines r for the configuration of FIG. 8, wherein 2A is the distance between load cells 118 in weighing station 28. Equations (3) and (4) in Appendix A show the resolution of the centrifugal force in the x ($F_x$) and y ($F_y$) directions of FIG. 8.

If the leftmost rack tray in FIG. 8 is referred to a the $x^-$ rack tray and the rightmost rack tray is referred to as the $x^+$ rack tray, and the mass of a rack i which is in the positive y direction, relative to the rotor hub, is referred to as $m_{iy+}$ and the mass of that rack i which is in the negative y direction, relative to the rotor hub, is referred to as $m_{iy-}$, then the total forces in the x and y directions can be written as shown in equations (5) through (8) in Appendix A.

Adding equations (5) and (7) to obtain the net force in the x axis directions yields equation (9) or (10) in Appendix A. If we define $m_{x+}$ and $m_{x-}$ as shown in equations (11) and (12) in appendix A, equation (10) can be simplified as shown in equation (13). In a similar manner, equation (14) can be derived for the net force in the direction of the y axis.

These net forces are the imbalance forces experienced at the rotor hub and, as will be apparent, corresponding imbalance masses can be derived by substituting equations (13) and (14) into equation (1) and solving for m as shown in equations (15) and (16) in Appendix A. As r is a constant, equation (17) in Appendix A is equivalent to equation (16) and is in a more convenient form for subsequent discussion.

As will be apparent, it is desired to minimize equation (17). It will also be apparent that the $m_{x+}$ and $m_{x-}$ terms in equation (17) are entirely independent from the $m_{y+}$ and $m_{y-}$ terms, the former being dictated solely by the rack tray into which the sample holding rack is placed and the latter being dictated solely by the orientation of the sample holding racks in the rack trays. Accordingly, the minimization of equation (17) can be split into two independent tasks, the minimization of $|m_{x+}-m_{x-}|$ and the minimization of $|m_{y+}-m_{y-}|$.

To minimize $|m_{x+}-m_{x-}|$ we place a first sample holding rack into an arbitrary slot 56 of one rack tray 44. Then, assuming that, as in the embodiment shown in the Figures, there are two rack trays 44 each having four slots 56, for a total of eight sample holding racks, there are thirty five combinations in which three of the remaining seven sample holding racks may be loaded into rack tray 44. These combinations are shown in Appendix B wherein the first sample holding rack which was loaded into rack tray 44 is identified by the reference numeral 1, and the remaining sample holding trays are identified by the arbitrarily assigned reference numerals 2 through 8.

As will be clear, all that need be done now is to compute the value of $|m_{x+}-m_{x-}|$ for each of the thirty five possible groupings of sample holding racks listed in Appendix B.

To minimize $|m_{y+}-m_{y-}|$, it will be apparent that there are one hundred and twenty eight different arrangements in which the seven remaining sample holding racks (the first rack is loaded in an arbitrary orientation) can be positioned. Again, the minimization of $|m_{y+}-m_{y-}|$ is accomplished by calculating the value of $|m_{y+}-m_{y-}|$ for each of these one hundred and twenty eight arrangements.

Figure 9:
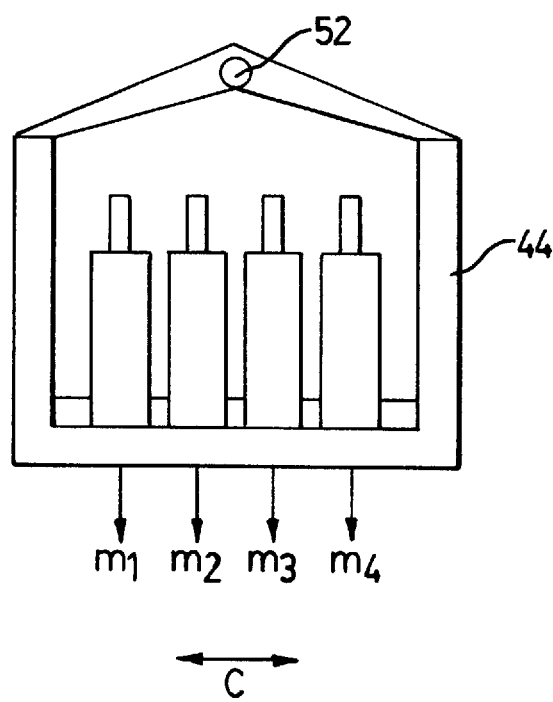
FIG. 9 shows a schematic representation of sample holding racks in a rack tray of the rotor.

While not essential in many circumstances, it can also be desirable to balance the loading of each rack tray 44 in the z-axis of FIG. 8. Equation (18) in Appendix A shows net moment M about the center of a rack tray 44, as shown in FIG. 9. In this discussion, the value $m_i$ denotes the total mass of sample holding rack i and C denotes the width of the rack tray 44. There are twenty four possible arrangements in which four sample holding racks can be placed in slots 56 of a rack tray 44. Accordingly, the value of M is determined for each of these arrangements and the arrangement with the lowest value for M is selected.

In use, centrifuge 20 receives eight sample holding racks via transport systems 94 and/or 98. These sample holding racks can arrive at substantially the same time or can arrive individually, in a random manner. In either case, each sample holding rack is weighed in weighing station 28 to obtain the two weight measurements for the rack and the respective weight measurements are communicated to controller 38. If the sample holding rack which has been weighed is the first sample holding rack to arrive, rack handling robot 36 loads it into a predefined slot 56. Subsequently arriving sample holding racks, except for the last, are weighed in weighing station 28, their respective determined weights being communicated to controller 38, and the sample holding racks are "parked" in a defined parking area 124 (FIG. 1) adjacent rack handling robot 36. When the last of the eight sample holding racks arrives, it is weighed in weighing station 28, its measured weights communicated to controller 38, and it is moved along conveyor 32 or 34 so that it is in a position wherein rack handling robot 36 can engage it.

Controller 38 now examines the measured weights of each sample holding rack and proceeds to identify the arrangement of the respective sample holding racks, given the arbitrary placement of the first sample holding rack, which minimizes each of $|m_{x+}-m_{x-}|$, $|m_{y+}-m_{y-}|$ and M. When this determination is completed, a best balance arrangement is known and rack handling robot 36 places the sample holding racks into slots 56 to obtain the best balance arrangement, removing the sample holding racks from parking zone 124 and from conveyor 32 or 34, as appropriate.

It is contemplated that in some circumstances, for example a sample holding rack with one or more empty samples, it may not be possible for controller 38 to achieve a balance within pre-defined values for one of $|m_{x+}-m_{x-}|$ and $|m_{y+}-m_{y-}|$, and optionally M. These predefined values would be selected depending upon the centrifuge's ability to safely handle out of balance loads. In the circumstance wherein these pre-determined values are exceeded, controller 38 can reject a sample holding rack under consideration and replace it with the next sample holding rack which arrives at centrifuge 20. The selection of which sample holding rack to reject from consideration can be random, but ideally will be based upon a comparison to statistical data relating to expected ranges of total weight and the expected ranges for the location of the center of gravity for sample holding racks. In this latter case, controller 38 can reject the sample holding rack under consideration which is furthest from the expected ranges.

A sample holding rack which has been rejected can be placed into parking zone 124 for consideration as one of the next eight sample holding racks to be processed. If a sample holding rack is rejected by controller 38 more than a pre-defined number of times, the sample holding rack will be placed in parking zone 124 and controller 38 will generate an appropriate alarm to a laboratory technician while processing of other sample holding racks continues.

It is contemplated that, for improved throughput or sample lifetime reasons, it may not always be desirable to await the arrival of eight sample holding racks before commencing centrifuging of the samples. In such as situation, as may be determined by a timer in controller 38, by manual direction of a laboratory technician, or in any other suitable manner as may occur to those of skill in the art, one or more balancing racks may be maintained in parking zone 124 for use to complete a load of sample holding racks. It is also contemplated that, when a sample holding rack has been rejected, a balance rack may be substituted for it by controller 38 to allow timely processing of the remaining sample holding racks.

If a single balancing rack is employed, then the balancing method proceeds as before, with the balancing rack being considered as the eighth sample holding rack. The weight of the balancing rack, and its center of gravity, is not particularly limited, but should be within the expected range for arriving sample holding racks and will have been determined and communicated to controller 38 previously.

A more interesting case occurs when two or more balancing racks are maintained in parking area 124. In this case, the above described balancing method can be performed once with each available balancing rack and with the overall best balance arrangement being selected by controller 38. Once this overall best balance arrangement is selected, loading of centrifuge 20 with the sample holding racks proceeds and controller 38 operates rack handling robot 36 to load the appropriate balancing rack.

In this case, wherein multiple balance racks are available, it can be advantageous to provide one or more balance racks with total weights somewhat outside the expected normal ranges, and with centers of gravity being located outside the expected normal ranges. This can allow for acceptable balancing to be achieved for a wider range of sample holding racks and a reduction in the number of rejected racks, as mentioned above.

Once a centrifuge operation has been completed, as determined for example by the expiry of a predefined time at the selected centrifuge speed, rotor 40 is braked to a stop in the position shown in FIG. 3 and rack handling robot 36 removes the sample holding racks from slots 56 and places them onto the outbound portions of transport systems 94 or 98. Also, any balance racks which have been employed are returned to parking zone 124.

To minimize the number of movements of gripper 60 required for loading and unload of rack trays 44, and thus improve throughput, controller 38 can operate rack handling robot 36 such that after the transfer of one processed sample holding rack from rotor 40 to one of transport systems 94 or 94, are performed cycles wherein robot 36 transfers a sample holding rack awaiting processing into a slot 56 in rotor 40 and then transfers a processed sample holding rack from another slot 56 in rotor 40 to one of transport systems 94 or 98. These cycles continue until the last processed sample holding rack is removed and then rack handling robot 36 completes the loading/unloading operation by transferring the last sample holding rack to be processed to the last empty slot 56. Of course, throughout this loading/unloading process, rack handling robot 36 is loading sample holding racks according to the best balance arrangement determined by controller 38.

The present invention provides a novel automated centrifuge which is operable to automatically load, process and unload sample holding racks without requiring constant laboratory technician assistance. The unique balance method disclosed allows the automatic loading to achieve a load of sample holding racks which is balanced within a predefined set of balance threshold values. It is contemplated that the present invention will reduce the labour costs associated with the centrifuging of samples and the resulting loads of sample holding racks will not exceed predetermined balance thresholds, thus allow a manufacturer to employ components with a reduced tolerance to off balance conditions, consequently reducing manufacturing costs.

The above-described embodiments of the invention are intended to be examples of the present invention and alterations and modifications may be effected thereto, by those of skill in the art, without departing from the scope of the invention which is defined solely by the claims appended hereto.

Appendix A $$F = m\omega^2 r \qquad (1)$$

$$r = \sqrt{A^2 + B^2} \qquad (2)$$

$$F_x = m\cos\left(\tan^{-1}\left(\frac{A}{B}\right)\right)\omega^2 r = Bm\omega^2 \qquad (3)$$

$$F_y = m\sin\left(\tan^{-1}\left(\frac{A}{B}\right)\right)\omega^2 r = Am\omega^2 \qquad (4)$$

$$F_{x_{x^-}} = -\sum_{i \in x^-} m_i B \omega^2 \qquad (5)$$

$$F_{y_{x^-}} = \sum_{i \in x^-} m_{i_{y^+}} A\omega^2 - \sum_{i \in x^-} m_{i_{y^-}} A\omega^2 = \sum_{i \in x^-} (m_{i_{y^+}} - m_{i_{y^-}})A\omega^2 \qquad (6)$$

$$F_{x_{x^+}} = \sum_{i \in x^+} m_i B \omega^2 \qquad (7)$$

$$F_{y_{x^+}} = \sum_{i \in x^+} m_{i_{y^+}} A\omega^2 - \sum_{i \in x^+} m_{i_{y^-}} A\omega^2 = \sum_{i \in x^+} (m_{i_{y^+}} - m_{i_{y^-}})A\omega^2 \qquad (8)$$

$$F_{net_2} = F_{x_{x^+}} + F_{x_{x^-}} \qquad (9)$$

$$F_{net_x} = \sum_{i \in x^+} m_i B \omega^2 - \sum_{i \in x^-} m_i B \omega^2 \qquad (10)$$

$$m_{x^+} = \sum_{i \in x^+} m_i \qquad (11)$$

$$m_{x^-} = \sum_{i \in x^-} m_i \qquad (12)$$

$$F_{net_x} = (m_{x^+} - m_{x^-})B\omega^2 \qquad (13)$$

$$F_{net_y} = (m_{y^+} - m_{y^-})A\omega^2 \qquad (14)$$

$$m_{imbalance} = \frac{\sqrt{F_{net_x}^2 + F_{net_y}^2}}{\omega^2 B} \qquad (15)$$

$$m_{imbalance} = \frac{\sqrt{B^2(m_{x^+} - m_{x^-})^2 + A^2(m_{y^+} - m_{y^-})^2}}{B} \qquad (16)$$

$$(rm_{imbalance})^2 = B^2(m_{x^+} - m_{x^-})^2 + A^2(m_{y^+} - m_{y^-})^2 \qquad (17)$$

$$M = \frac{3}{2}Cm_1 + \frac{1}{2}Cm_2 - \frac{1}{2}Cm_3 - \frac{3}{2}Cm_4 \qquad (18)$$

Appendix B

-continued (1, 2, 3, 4), (1, 2, 3, 5), (1, 2, 3, 6), (1, 2, 3, 7), (1, 2, 3, 8),
(1, 2, 4, 5), (1, 2, 4, 6), (1, 2, 4, 7), (1, 2, 4, 8),
(1, 2, 5, 6), (1, 2, 5, 7), (1, 2, 5, 8),
(1, 2, 6, 7), (1, 2, 6, 8),
(1, 2, 7, 8),
(1, 3, 4, 5), (1, 3, 4, 6), (1, 3, 4, 7), (1, 3, 4, 8),
(1, 3, 5, 6), (1, 3, 5, 7), (1, 3, 5, 8),
(1, 3, 6, 7), (1, 3, 6, 8),
(1, 3, 7, 8),
(1, 4, 5, 6), (1, 4, 5, 7), (1, 4, 5, 8),
(1, 4, 6, 7), (1, 4, 6, 8),
(1, 4, 7, 8),
(1, 5, 6, 7), (1, 5, 6, 8),
(1, 5, 7, 8),
(1, 6, 7, 8)

We claim:

1. An automated centrifuge for processing samples loaded into sample holding racks, said centrifuge comprising:
    a weighing station to determine, for each sample holding rack delivered to said centrifuge, the mass of said sample holding rack, and the center of gravity of said sample holding rack relative to the longitudinal axis of said sample holding rack;
    a centrifuge rotor having an axis of rotation and being operable to receive and centrifuge a plurality of said sample holding racks;
    a controller to determine a loading arrangement for said weighed sample holding racks which results in the balancing of said centrifuge rotor about said axis of rotation within at least one predefined threshold when said centrifuge rotor is loaded with said weighed sample holding racks; and
    a rack transfer means to load and unload weighed sample holding racks in said centrifuge rotor, said weighed sample holding racks being loaded in an arrangement corresponding to said determined loading arrangement.

2. An automated centrifuge according to claim 1 wherein each said sample holding rack can hold at least two samples to be processed by said centrifuge.

3. An automated centrifuge according to claim 2 further comprising a transport system to deliver said sample holding racks to said rack transfer means for processing in said centrifuge and to remove sample holding racks which have been processed by said centrifuge from said rack transfer means.

4. An automated centrifuge according to claim 3 further including a parking area in which sample holding racks delivered by said transport system are stored after weighing until a preselected number of sample holding racks have been delivered to said centrifuge when said rack transfer means loads said centrifuge in said determined loading arrangement.

5. An automated centrifuge according to claim 4 further including at least one balancing rack stored in said parking area for loading into said centrifuge rotor in place of a sample holding rack, if less than said preselected number of sample holding racks is delivered to said centrifuge in a predefined time, said sample holding racks and said at least one balancing rack totalling said preselected number.

6. An automated centrifuge according to claim 4 wherein said rack transfer means is operable to load sample holding racks into said centrifuge rotor for processing while removing processed sample holding racks therefrom.

7. A method of determining an arrangement of a preselected number of sample holding racks to be loaded into a rotor of a centrifuge, said arrangement resulting in the balancing of said rotor about the axis of rotation thereof within a predefined threshold when said rotor is loaded with said sample holding racks, comprising the steps of:
    (i) weighing each of said preselected number of sample holding racks to be loaded into said rotor, said weighing determining the total weight and the center of gravity of each sample holding rack with respect to the longitudinal axis of each sample holding rack;
    (ii) examining said determined total weight of each sample holding rack and selecting two subsets of equal numbers of said preselected number of sample holding racks, said two subsets being selected such that the difference between the total of the weights of the sample holding racks in each said selected subset is less than a pre-defined threshold; and
    (iii) examining each said selected subset to determine the orientation of the sample holding racks in each said subset such that the net distance of the determined centers of gravity of the sample holding racks in a subset from the midpoint of the sample holding racks is less than a pre-defined threshold.

8. The method of claim 7 further comprising the steps of loading said sample holding racks into said rotor such that each rack of each said selected subset is in said determined orientation, and processing said racks within said centrifuge.

9. The method of claim 8 further comprising the step of placing each said weighed sample holding rack into a parking area adjacent said rotor until said preselected number of sample holding racks have accumulated therein before loading said sample holding racks into said rotor.

10. The method of claim 9 wherein at least one balancing rack is available in said parking area, said at least one balancing rack being weighed and loaded into said rotor in place of a sample holding rack.

11. The method of claim 10 wherein said at least one balancing rack is employed when less than said preselected number of sample holding racks is available for processing within a predetermined time period.

12. The method of claim 10 wherein at least two balancing racks are available in said parking area, each said balancing rack having a different center of gravity from the other of said at least two balancing racks, and further comprising the step of selecting and orienting one of said at least two balancing racks to be loaded into said rotor in place of a sample holding rack to further reduce the net distance of the determined centers of gravity of said sample holding racks and said selected balancing rack from said midpoint of said sample holding racks.

13. The method of claim 8 further comprising the steps of automatically receiving said sample holding racks for processing from a transport system, and automatically removing processed sample holding racks with a transport system.

14. A method of loading a rotor of a centrifuge with a preselected number of sample holding racks in an arrangement which results in the balancing of said rotor about the axis of rotation thereof within at least one predefined threshold, wherein said rotor comprises two sample holding rack receiving trays which are diametrically opposed about the axis of rotation, comprising the steps of:
    (i) receiving said preselected number of sample holding racks to be loaded into said rotor;
    (ii) weighing each of said received sample holding racks, said weighing determining the total weight of each said sample holding rack and the center of gravity of each said sample holding rack with respect to the longitudinal axis of said sample holding rack;

(iii) examining said determined total weight of each said sample holding rack and selecting two subsets of equal numbers of said sample holding racks from said preselected number of sample holding racks, said two subsets being selected such that the difference between the sum of the weights of the sample holding racks in each said selected subset is less than a pre-defined threshold; and (iv) examining each said selected subset to determine the orientation of the sample holding racks in each said subset such that the net distance of the centers of gravity of the sample holding racks in a subset is less than a pre-defined threshold; and (v) loading each said sample holding rack receiving tray with one determined subset, the sample holding racks in each determined subset being loaded in said determined orientation.

15. The method of claim 14 further comprising the steps of:

(vi) processing said loaded sample holding racks with said centrifuge; and (vii) transferring said processed sample holding racks from said sample holding rack trays to a transport system.

16. The method of claim 15 wherein each said sample holding rack is received and weighed in turn and placed in a parking area until all of said preselected number of sample holding racks have been received.

17. The method of claim 16 wherein said sample holding racks are loaded in said determined orientation sequentially by first transferring a processed sample holding rack from a position in said sample holding rack receiving tray and then loading a sample holding rack to be processed into said position in said sample holding rack receiving tray, said processing of said loaded sample holding racks being performed once all processed sample holding racks have been transferred from said sample holding rack receiving tray and replaced with said loaded sample holding racks.

18. The method of claim 16 further comprising at least one weighed balance rack placed in said parking area and wherein, when said preselected number of sample holding racks is not received within a preselected time period, said received sample holding racks are combined with said at least one weighed balance rack to obtain said preselected number of sample holding racks which are loaded into said rotor for processing, said at least one balance rack being returned to said parking area during transfer of said sample holding racks.

19. The method of claim 16 further comprising at least one weighed balance rack placed in said parking area and wherein, when said preselected number of sample holding racks can not be loaded in a determined orientation wherein said rotor is balanced within said at least one predefined threshold, said at least one weighed balance rack is substituted for a received sample holding rack and steps (iii) and (iv) are performed again, said substituted sample holding rack being placed in said parking area to form part of a next preselected number of sample holding racks.

20. The method of claim 14 wherein each said sample holding rack is received and weighed in turn and placed in a parking area until all of said preselected number of sample holding racks have been received.

* * * * *